United States Patent
Takami et al.

(10) Patent No.: US 12,161,387 B2
(45) Date of Patent: Dec. 10, 2024

(54) CONTROL DEVICE, TREATMENT SYSTEM, AND CONTROL METHOD

(71) Applicant: OLYMPUS CORPORATION, Hachioji (JP)

(72) Inventors: Sadayoshi Takami, Hachioji (JP); Tsuyoshi Hayashida, Hachioji (JP); Toshifumi Katsuragi, Hachioji (JP); Shohei Moriwaki, Akishima (JP); Yoshitaka Honda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 740 days.

(21) Appl. No.: 17/363,531

(22) Filed: Jun. 30, 2021

(65) Prior Publication Data

US 2021/0322090 A1 Oct. 21, 2021

Related U.S. Application Data

(63) Continuation of application No. PCT/JP2019/001144, filed on Jan. 16, 2019.

(51) Int. Cl.
*A61B 18/12* (2006.01)
*A61B 18/14* (2006.01)
(Continued)

(52) U.S. Cl.
CPC ............ *A61B 18/1445* (2013.01); *A61B 2018/00648* (2013.01); *A61B 2018/00702* (2013.01);
(Continued)

(58) Field of Classification Search
CPC ............ A61B 18/1206; A61B 18/1445; A61B 2018/00648; A61B 2018/00666;
(Continued)

(56) References Cited

U.S. PATENT DOCUMENTS

| 2007/0123847 A1 | 5/2007 | Mihori |
| 2008/0114351 A1 | 5/2008 | Irisawa et al. |

(Continued)

FOREIGN PATENT DOCUMENTS

| JP | 2007-143878 A | 6/2007 |
| JP | 2008-114042 A | 5/2008 |

(Continued)

OTHER PUBLICATIONS

Apr. 2, 2019 International Search Report issued in International Application No. PCT/JP2019/001144.

*Primary Examiner* — Daniel W Fowler
(74) *Attorney, Agent, or Firm* — Oliff PLC

(57) ABSTRACT

A control device includes: a power source configured to supply a high frequency power to a treatment instrument configured to treat a living tissue; a detecting circuit configured to sequentially detect a phase difference between a voltage and a current of the high frequency power supplied to the treatment instrument; and a processor configured to control operation of the power source, the processor being configured to sequentially calculate a variation of the phase difference detected by the detecting circuit, compare the calculated variation of the phase difference with a first threshold set for a variation of a phase difference, and perform reduction processing to reduce output of the high frequency power to be supplied to the treatment instrument when it is determined that the calculated variation of the phase difference is equal to or smaller than the first threshold.

12 Claims, 14 Drawing Sheets

(51) Int. Cl.
    *A61B 18/00* (2006.01)
    *A61B 90/00* (2016.01)
(52) U.S. Cl.
    CPC .............. *A61B 2018/00827* (2013.01); *A61B 2018/00875* (2013.01); *A61B 2018/00892* (2013.01); *A61B 2090/065* (2016.02)
(58) Field of Classification Search
    CPC .......... A61B 2018/00672; A61B 2018/00678; A61B 2018/00702; A61B 2018/00827; A61B 2018/00869; A61B 2018/00875; A61B 2018/00886; A61B 2018/00892
    See application file for complete search history.

(56) References Cited

U.S. PATENT DOCUMENTS

| | | |
|---|---|---|
| 2009/0306648 A1 | 12/2009 | Podhajsky et al. |
| 2010/0094276 A1 | 4/2010 | Kabaya et al. |
| 2014/0257269 A1* | 9/2014 | Woloszko ............ A61B 18/042 606/41 |
| 2016/0000495 A1 | 1/2016 | Elliott et al. |
| 2016/0374746 A1* | 12/2016 | Takami ............... A61B 18/1206 606/30 |
| 2017/0042604 A1* | 2/2017 | McFarland ........ A61B 18/1233 |

FOREIGN PATENT DOCUMENTS

| | | |
|---|---|---|
| JP | 2011-523888 A | 8/2011 |
| JP | 2017-515645 A | 6/2017 |
| WO | 2010/044354 A1 | 4/2010 |

* cited by examiner

CONTROL DEVICE, TREATMENT SYSTEM, AND CONTROL METHOD

CROSS-REFERENCE TO RELATED APPLICATION

This application is a continuation of International Application No. PCT/JP2019/001144, filed on Jan. 16, 2019, the entire contents of which are incorporated herein by reference.

BACKGROUND

1. Technical Field

The present disclosure relates to a control device, a treatment system, and a control method.

2. Related Art

A treatment system including a control device, and a treatment instrument that applies a high frequency energy to a living tissue, being supplied with a high frequency voltage and a high frequency current from the control device has been known (for example, JP-A-2007-143878).

A control device (high-frequency power source device) described in JP-A-2007-143878 includes a power source (high-frequency-power generating unit) that supplies a high frequency voltage and a high frequency current to a treatment instrument, a detecting circuit (phase detecting unit) that sequentially detects a phase difference of the high frequency voltage and the high frequency current being supplied to the treatment instrument from the power source, and a processor (control unit) that controls operation of the power source.

The processor controls outputs of the high frequency voltage and the high frequency current to the treatment instrument from the power source by using an absolute value of the phase difference detected by the detecting circuit.

SUMMARY

In some embodiments, a control device includes: a power source configured to supply a high frequency power to a treatment instrument configured to treat a living tissue; a detecting circuit configured to sequentially detect a phase difference between a voltage and a current of the high frequency power supplied to the treatment instrument; and a processor configured to control operation of the power source, the processor being configured to sequentially calculate a variation of the phase difference detected by the detecting circuit, compare the calculated variation of the phase difference with a first threshold set for a variation of a phase difference, and perform reduction processing to reduce output of the high frequency power to be supplied to the treatment instrument when it is determined that the calculated variation of the phase difference is equal to or smaller than the first threshold.

In some embodiments, a control device includes: a power source configured to supply a high frequency power to a treatment instrument configured to treat a living tissue; a detecting circuit configured to sequentially detect a voltage and a current of the high frequency power supplied to the treatment instrument; and a processor configured to control operation of the power source, the processor being configured to sequentially calculate a variation of an impedance of the living tissue based on the voltage and the current detected by the detecting circuit, compare the calculated variation of the impedance with a seventh threshold set for a variation of an impedance, and perform reduction processing to reduce output of the high frequency power to be supplied to the treatment instrument when it is determined that the calculated impedance is equal to or smaller than the seventh threshold.

In some embodiments, a treatment system includes: the control device; and a treatment instrument configured to apply a high frequency energy to a living tissue by being supplied with a voltage and a current from the control device.

In some embodiments, provided is a control method that is performed by a processor of a control device. The method includes: sequentially calculating a variation of a phase difference of a voltage and a current of a high frequency power supplied to a treatment instrument from a power source; comparing the calculated variation of the phase difference with a first threshold set for a variation of a phase difference; and performing reduction processing to reduce output of the high frequency power to be supplied to the treatment instrument when it is determined that the calculated variation of the phase difference is equal to or smaller than the first threshold.

In some embodiments, provided is a control method that is performed by a processor of a control device. The method includes: sequentially calculating a variation of an impedance of a living tissue based on a voltage and a current of a high frequency power supplied to a treatment instrument from a power source; comparing the calculated variation of the impedance with a seventh threshold set for an impedance; and performing reduction processing to reduce output of the high frequency power to be supplied to the treatment instrument when it is determined that the calculated variation of the impedance is equal to or smaller than the seventh threshold.

The above and other features, advantages and technical and industrial significance of this invention will be better understood by reading the following detailed description of presently preferred embodiments of the disclosure, when considered in connection with the accompanying drawings.

DETAILED DESCRIPTION

Hereinafter, forms to implement the disclosure (hereinafter, embodiments) will be explained with reference to the drawings. Embodiments described in the following are not intended to limit the disclosure. Furthermore, like reference symbols are assigned to like parts throughout the drawings.

First Embodiment

Schematic Configuration of Treatment System

Figure 1:
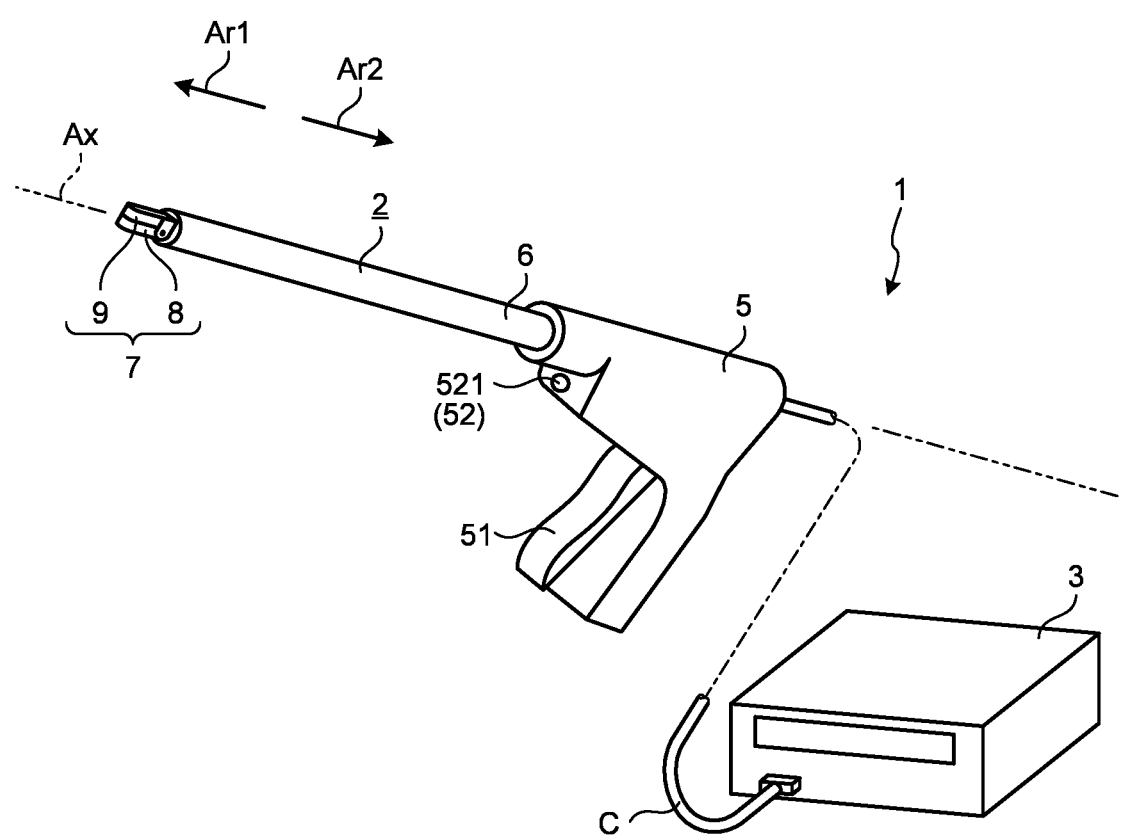
FIG. 1 is a diagram illustrating a treatment system according to an exemplary embodiment.

FIG. 1 is a diagram illustrating a treatment system 1 according to a first embodiment.

The treatment system 1 applies a treatment energy to an area targeted for treatment (hereinafter, target area) in a living tissue, to treat the target area. In the first embodiment, a high frequency energy is used as the treatment energy. Moreover, examples of the treatment include sealing or incision of the target area.

This treatment system 1 includes a treatment instrument 2 and a control device 3 as illustrated in FIG. 1.
Configuration of Treatment Instrument The treatment instrument 2 is a surgical treatment instrument to treat a target area, for example, through an abdominal wall. This treatment instrument 2 includes a handle 5, a sheath 6, and a grabbing portion 7 as illustrated in FIG. 1.

The handle 5 is a portion held by an operator with hands. In this handle 5, an operating knob 51 and an interface 52 are provided as illustrated in FIG. 1.

The interface 52 is arranged to be exposed outside from the handle 5, and includes a switch 521 (FIG. 1) to accept an output start operation by the operator. The switch 521 outputs an operation signal according to the output start operation to the control device 3 through an electric cable C (FIG. 1).

The sheath 6 has a substantially cylindrical shape. In the following, for convenience of explanation, one side (left side in FIG. 1) along the center axis Ax (FIG. 1) of the sheath 6 is denoted as a distal end side Ar1, and the other side (right side in FIG. 1) is denoted as a proximal end side Ar2. This sheath 6 is connected to the handle 5 at its end portion on the proximal end side Ar2 (FIG. 1). Moreover, to an end portion of the sheath 6 on the distal end side Ar1, the grabbing portion 7 is attached. Inside the sheath 6, an opening closing mechanism (not illustrated) to open and close a first and a second grabbing members 8, 9 (FIG. 1) constituting the grabbing portion 7 is arranged. Furthermore, inside the sheath 6, the electric cable C is laid from the end portion on the proximal end side Ar2 to the end portion on the distal end side Ar1 through the handle 5.

Structure of Grabbing Portion

Figure 2:
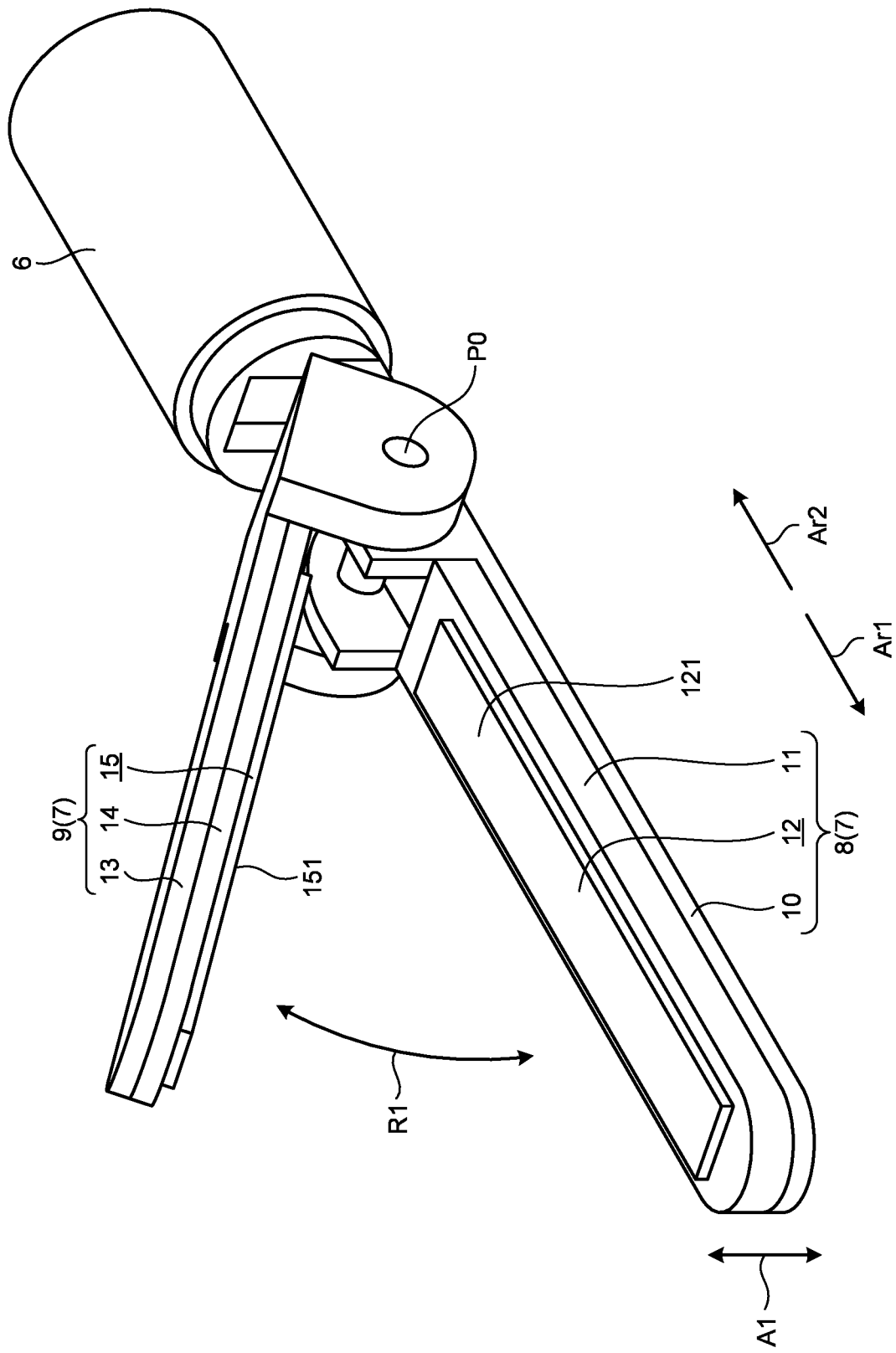
FIG. 2 is a diagram illustrating a grabbing portion.

FIG. 2 is a diagram illustrating the grabbing portion 7.

The grabbing portion 7 is a portion to treat the target area in a state in which the target area is grabbed. This grabbing portion 7 includes the first and the second grabbing members 8, 9 as illustrated in FIG. 1 or FIG. 2.

The first and the second grabbing members 8, 9 are structured to be openable and closable in a direction of an arrow R1 (FIG. 2) according to an operation of the operating knob 51 by an operator.
Structure of First Grabbing Member The first grabbing member 8 is arranged at a position facing the second grabbing member 9. This first grabbing member 8 includes a first jaw 10, a first supporting member 11, and a first electrode 12 as illustrated in FIG. 2.

The first jaw 10 is a portion formed by extending a portion of the sheath 6 on the distal end side Ar1, and is formed in a long shape extending in a longitudinal direction from a distal end toward a proximal end of the grabbing portion 7. This first jaw 10 is made from a metallic material, such as stainless and titanium. The first jaw 10 supports the first supporting member 11 and the first electrode 12.

The first supporting member 11 is a flat plate in a long shape extending in the longitudinal direction of the grabbing portion 7, and is made from, for example, a resin material having a low thermal conductivity, such as poly ether ether ketone (PEEK). The first supporting member 11 is arranged between the first jaw 10 and the first electrode 12.

The first electrode 12 is a plate-shaped member extending in the longitudinal direction of the grabbing portion 7, and is made from a conductive material, such as copper.

In this first electrode 12, a surface on a side of the second grabbing member 9 functions as a first grabbing surface 121 (FIG. 2) to grab a target area between itself and the second grabbing member 9. In the first embodiment, the first grabbing surface 121 is constituted of a flat surface perpendicular to a direction A1 (FIG. 2) in which the first and the second grabbing members 8, 9 face each other in a state in which the first and the second grabbing members 8, 9 grab the target area. The first grabbing surface 121 is constituted of a flat surface, but it may be formed in other shapes, such as a convex shape or a concave shape, not limited thereto. The same applied to a second grabbing surface 151 described later also.

Moreover, to the first electrode 12, a lead C1, which is one of a pair of leads C1, C1' (refer to FIG. 3) constituting the electric cable C, is connected.
Structure of Second Grabbing Member The second grabbing member 9 includes a second jaw 13, a second supporting member 14, and a second electrode 15 as illustrated in FIG. 2.

The second jaw 13 has a long shape extending in the longitudinal direction of the grabbing portion 7. The second jaw 13 is axially supported at its end portion on the proximal end side Ar2 in a rotational manner relative to the sheath 6 pivoted on a pivot P0 (FIG. 2), and opens and closes with respect to the first grabbing member 8 as it rotates.

Although a structure in which the first grabbing member 8 is fixed to the sheath 6, and the second grabbing member 9 is axially supported by the sheath 6 is applied in the first embodiment, it is not limited thereto. For example, a structure in which both the first and the second grabbing members 8, 9 may be axially supported by the sheath 6, and the first and the second grabbing members 8, 9 open and close as the both members rotate may be applied. Furthermore, for example, a structure in which the first grabbing member 8 is axially supported by the sheath 6, and the second grabbing member 9 is fixed to the sheath 6, and the first grabbing member 8 opens and closes with respect to the second grabbing member 9 as the first grabbing member 8 rotates may be applied.

The second supporting member 14 is made from a resin material having a low thermal conductivity, such as PEEK, and is arranged between the second jaw 13 and the second electrode 15.

The second electrode 15 is made from a conductive material, such as copper, and is fixed on a surface facing the first grabbing member 8 in the second supporting member 14.

In this second electrode 15, a surface on a side of the first grabbing member 8 functions as the second grabbing surface 151 to grab a target area between itself and the first grabbing surface 121. Moreover, to the second electrode 15, the other lead C1' is connected.

Configuration of Control Device

Figure 3:
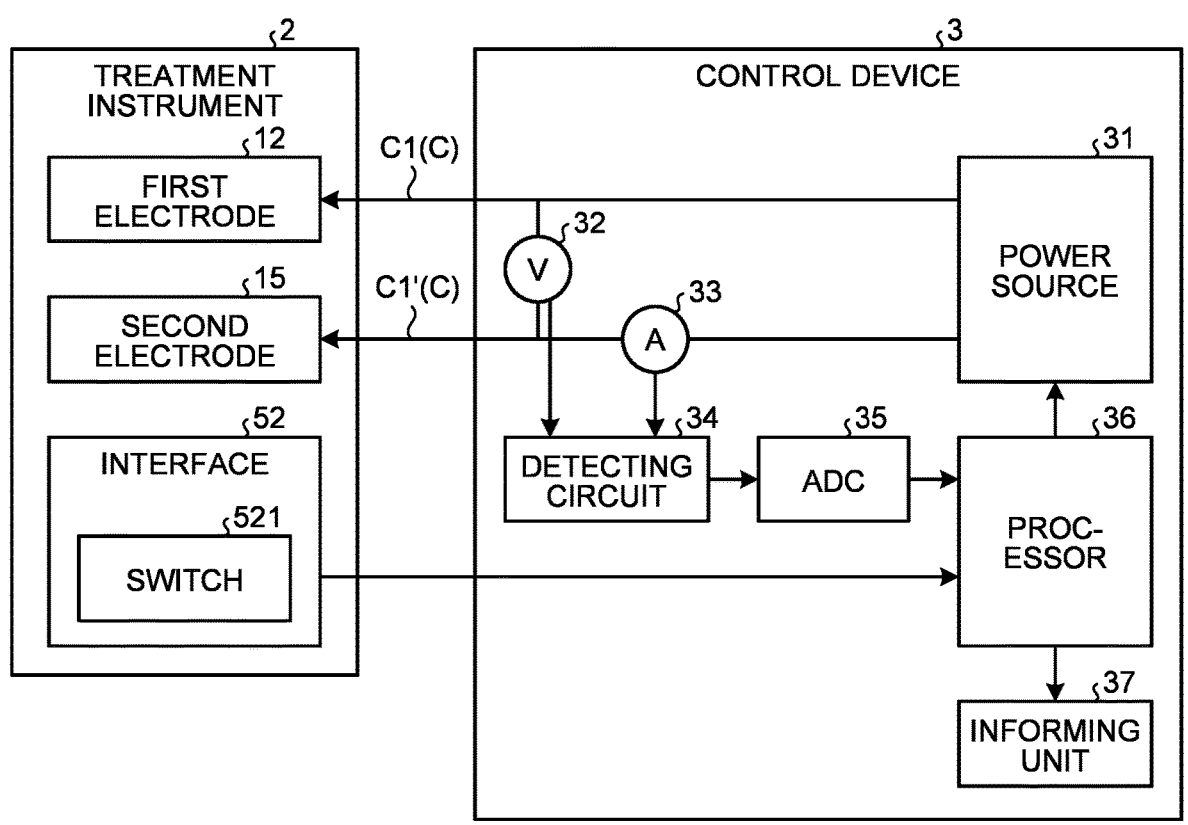
FIG. 3 is a block diagram illustrating a configuration of a control device.

FIG. 3 is a block diagram illustrating a configuration of the control device 3.

The control device 3 controls operations of the treatment instrument 2 in a centralized manner. This control device 3 includes, as illustrated in FIG. 3, a power source 31, a voltage detecting unit 32, a current detecting unit 33, a detecting circuit 34, an analog to digital converter (ADC) 35, a processor 36, and an informing unit 37.

The power source 31 supplies a high frequency voltage and a high frequency current to the first and the second electrodes 12, 15 through the pair of leads C1, C1' under control of the processer 36. Thus, to a target area grabbed between the first and the second electrodes 12 and 15, a high frequency current flows. In other words, to the target area, a high frequency energy is applied.

The voltage detecting unit 32 sequentially detects a high frequency voltage supplied to the first and the second electrodes 12, 15 from the power source 31 through the pair of leads C1, C1'. The voltage detecting unit 32 outputs an HF voltage signal according to the detected high frequency voltage to the detecting circuit 34.

The current detecting unit 33 sequentially detects a high frequency current supplied to the first and the second electrodes 12, 15 from the power source 31 through the pair of leads C1, C1'. The current detecting unit 33 outputs an HF current signal according to the detected high frequency current to the detecting circuit 34.

The detecting circuit 34 sequentially detects an HF phase difference θ (corresponds to "phase difference of a high frequency voltage and a high frequency current") between the HF voltage signal output from the voltage detecting unit 32 and the HF current signal output from the current detecting unit 33. The detecting circuit 34 sequentially outputs an HF phase-difference signal (analog signal) according to the detected HF phase difference θ to the ADC 35. Moreover, the detecting unit 34 sequentially outputs also an HF voltage signal (analog signal) output from the voltage detecting unit 32 and an HF current signal (analog signal) output from the current detecting unit 33 to the ADC 35.

The ADC 35 converts the HF phase-difference signal (analog signal), the HF voltage signal (analog signal), and the HF current signal (analog signal) output from the detecting circuit 34 into digital signals, to output to the processor 36.

The processor 36 is, for example, a central processing unit (CPU), a field programmable gate array (FPGA), or the like, and controls overall operations of the treatment system 1 according to a program stored in a memory (not illustrated). Detailed functions of the processor 36 will be described later in "Control Method Performed by Processor".

The informing unit 37 informs of predetermined information under control of the processor 36. Examples of this informing unit 37 include a light emitting diode (LED) that informs of predetermined information by lighting and flashing, or by colors of light, a display device that displays predetermined information, a speaker that outputs predetermined information with sound, and the like. The informing unit 37 may be provided in the control device 3 as illustrated in FIG. 3, or may be provided in the treatment instrument 2.

Control Method Performed by Processor

Next, a control method performed by the processor 36 will be explained.

Figure 4:
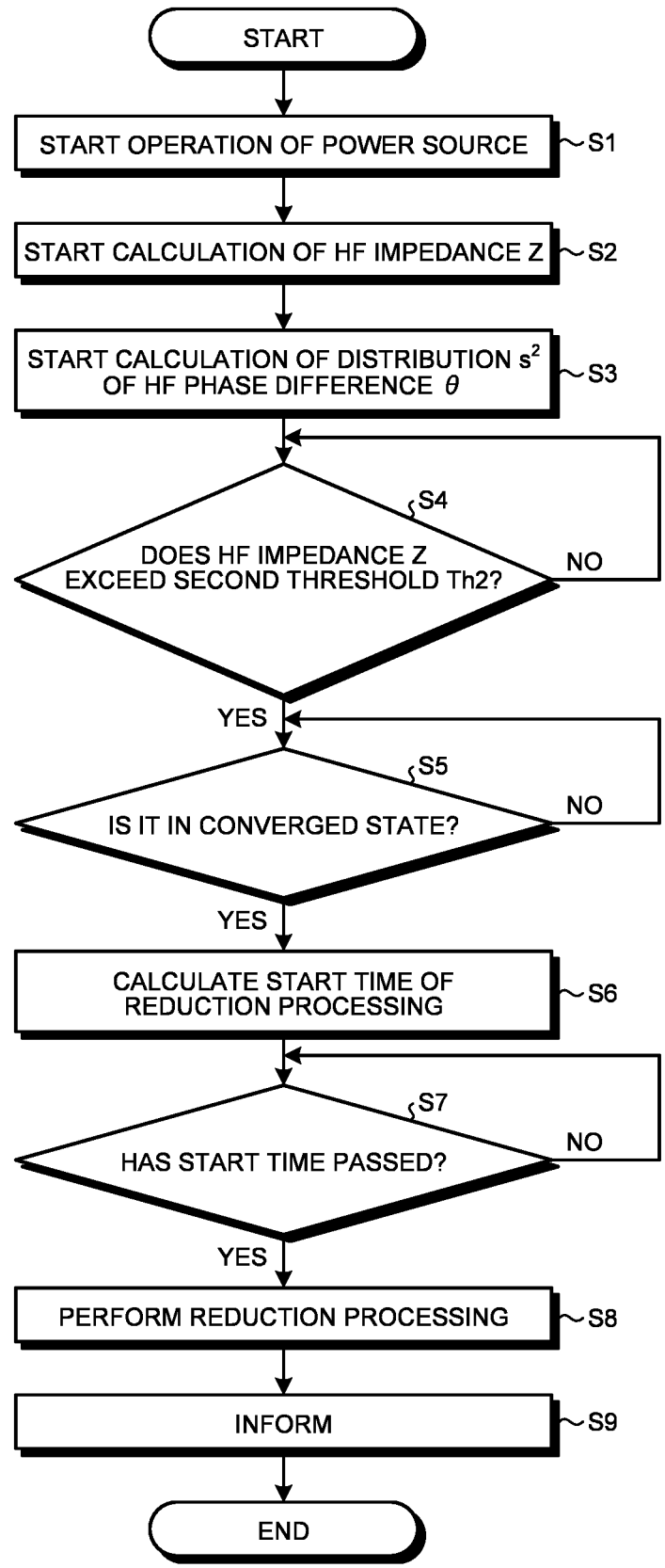
FIG. 4 is a flowchart illustrating a control method performed by a processor.

FIG. 4 is a flowchart illustrating the control method performed by the processor 36.

In the following, a control method of incising a target area grabbed between the first and the second electrodes 12 and 15 will be explained for convenience of explanation.

First, the processor 36 starts operation of the power source 31 according to a program stored in a memory (not illustrated) in accordance with an output start operation made with respect to a switch 521 by an operator (step S1). Thus, the power source 31 starts supplying a high frequency voltage and a high frequency current to the first and the second electrodes 12, 15 through the pair of leads C1, C1'. To the target area grabbed between the first and the second electrodes 12 and 15, a high frequency energy is started to be applied. Moreover, the voltage detecting unit 32, the current detecting unit 33, and the detecting circuit 34 start detection of the high frequency voltage and the high frequency current supplied to the first and the second electrodes 12, 15 from the power source 31, and the HF phase difference θ. That is, the detecting circuit 34 starts outputting the HF voltage signal, the HF current signal, and the HF phase-difference signal.

After step S1, the processor 36 starts calculation of an impedance value (hereinafter, HF impedance Z) of the target area grabbed between the first and the second electrodes 12 and 15 based on the HF voltage signal and the HF current signal that have been output from the detecting circuit 34, and have come through the ADC 35 (step S2).

Figure 5:
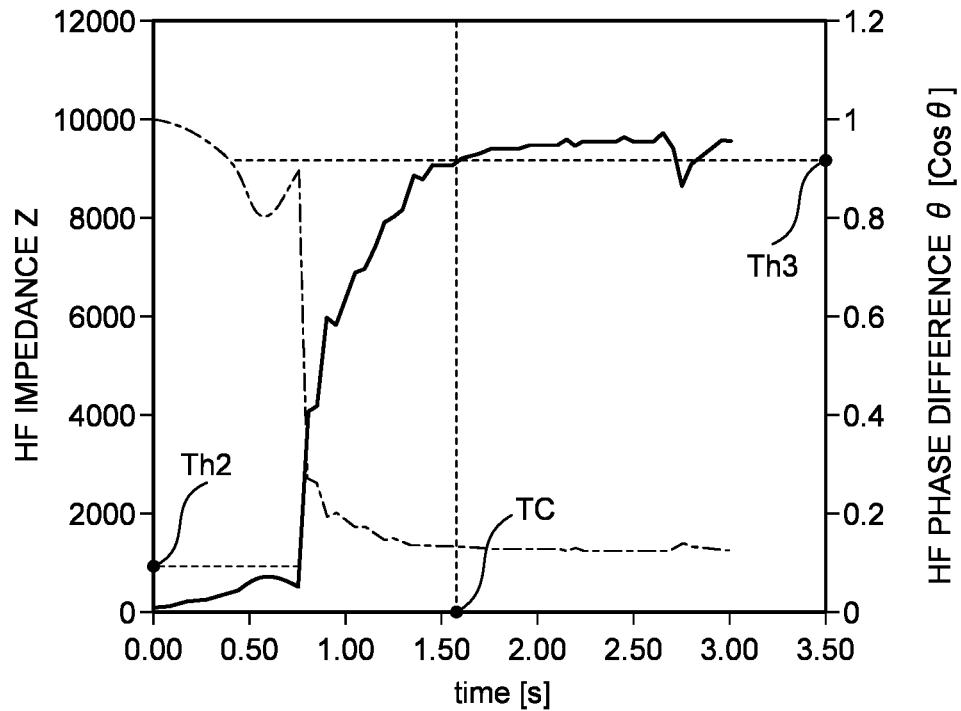
FIG. 5 is a diagram illustrating behaviors of an HF phase difference θ and an HF impedance Z at the time of performing the control method illustrated in FIG. 4.

FIG. 5 is a diagram illustrating behaviors of the HF phase difference θ and the HF impedance Z at the time of performing the control method illustrated in FIG. 4. In FIG. 5, a behavior of the HF phase difference θ is indicated by a dot-and-dash line, and the HF impedance Z is indicated by a solid line. Moreover, in FIG. 5, a behavior of the HF phase difference θ is expressed by Cos θ. The HF phase difference θ described below also signifies Cos θ. Furthermore, in FIG. 5, time TC indicates a time at which incision of a target area is completed.

The HF impedance Z shows a following behavior at an initial stage of application of the high frequency energy to the target area.

Specifically, the HF impedance Z gradually decreases, and becomes a minimum value when water of the target area is brought to a boil state. Moreover, if application of the high frequency energy is further continued, the HF impedance Z returns to increase because water in the target area evaporates. Note that because the order of vertical axis is large in FIG. 5, the behavior of the HF impedance Z in the initial stage described above is not sufficiently shown.

After the initial stage described above, the HF impedance Z abruptly increases as the target area is started to be incised as illustrated in FIG. 5, and then converges.

On the other hand, the HF phase difference θ gradually decreases from 1 (0°) as illustrated in FIG. 5 when application of the high frequency energy to the target area is started. Furthermore, the HF phase difference θ abruptly decreases as incision of the target area is started, and then converges to near 0 (near 90°).

After step S1, the processor 36 starts calculation of variation of the HF phase difference θ detected by the detecting circuit 34 (step S3). In FIG. 4, it is illustrated as step S3 is performed after step S2 for convenience of explanation, but step S2 and step S3 are performed substantially at the same time in an actual situation.

In the first embodiment, the processor 36 calculates a distribution $s^2$ of the HF phase difference θ as a variation of the HF phase difference θ. Specifically, the processor 36 calculates the distribution $s^2$ of the HF phase difference θ by following Equation (1). In Equation (1), n indicates the number of data (HF phase difference θ) at the time of acquiring the distribution $s^2$, and is 3 or larger. $x_i$ is a value of each data (HF phase difference θ).

$$s^2 = \frac{1}{n}\sum_{i=1}^{n}(x_i - \bar{x})^2 \quad (1)$$

$$\bar{x} = \frac{1}{n}\sum_{i=1}^{n}x_i$$

Figure 6:
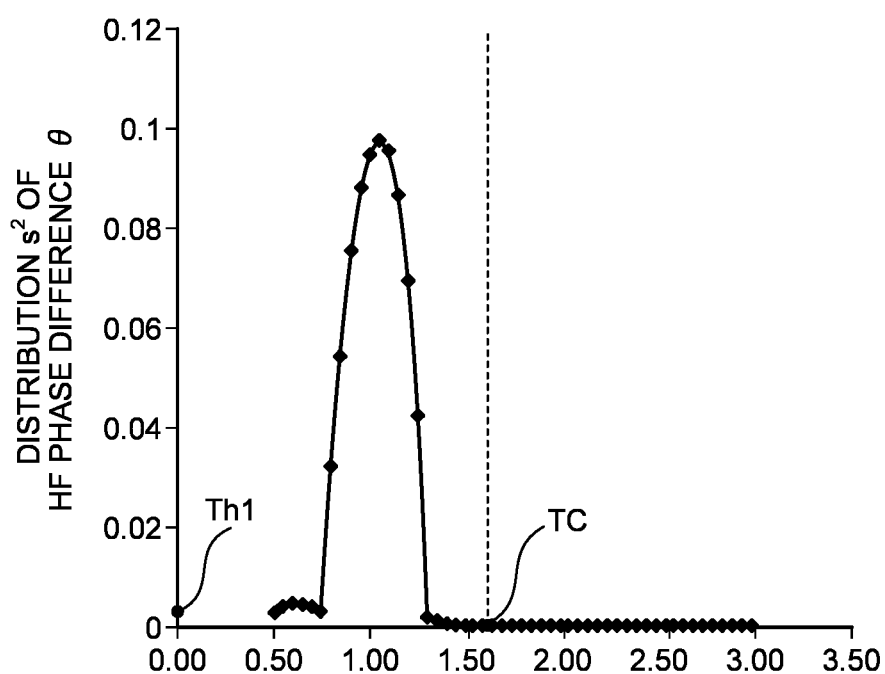
FIG. 6 is a diagram illustrating a behavior of a distribution $s^2$ of the HF phase difference θ at the time of performing the control method illustrated in FIG. 4.

FIG. 6 is a diagram illustrating a behavior of the distribution $s^2$ of the HF phase difference θ at the time of performing the control method illustrated in FIG. 4. Specifically, FIG. 6 shows a behavior of the distribution $s^2$ of the HF phase difference θ corresponding to the HF phase difference θ shown in FIG. 5. Moreover, the distribution $s^2$ of the HF phase difference θ shown in FIG. 6 is obtained by acquiring 10 samples of the HF phase differences θ detected every 50 ms in 500 ms, and by calculating with the 10 samples of the HF phase differences θ by Equation (1). That is, when a current time is 500 ms, the distribution $s^2$ of the HF phase difference θ at the current time (500 ms) is calculated with 10 samples of the HF phase differences θ including the HF phase difference θ at 50 ms (n=1) and the HF phase difference θ at 100 ms (n=2), . . . and the HF phase difference θ at 500 ms (n=10) by using Equation (1). Moreover, when the current time is 550 ms, the distribution $s^2$ of the HF phase difference θ at the current time (550 ms) is calculated with 10 samples of the HF phase differences θ including the HF phase difference θ at 100 ms (n=1) and the HF phase difference θ at 150 ms (n=2), . . . and the HF phase difference θ at 550 ms (n=10) by using Equation (1). Note that n is not limited to 10, but it may be 3 or more. Moreover, the sampling cycle of the HF phase difference θ to be used for calculation of the distribution $s^2$ of the HF phase difference θ is not limited to 50 ms, but it may be other cycles.

The distribution $s^2$ of the HF phase difference θ abruptly increases as incision of a target area is started as shown in FIG. 6, and abruptly decreases as the incision of the target area approaches its completion, and thereafter converges.

After step S3, the processor 36 monitors all the time whether the HF impedance Z exceeds a second threshold Th2 (FIG. 5) (step S4).

When it is determined that the HF impedance Z exceeds the second threshold Th2, (step S4: YES), the processor 36 determines all the time whether it has become a converged state in which the distribution $s^2$ of the HF phase difference θ has converged, by comparing the distribution $s^2$ of the HF phase difference θ with a first threshold Th1 (FIG. 6) (step S5). In the present embodiment, the processor 36 determines that it has become the converged state when the distribution $s^2$ of the HF phase difference θ becomes equal to or smaller than the first threshold Th1. On the other hand, the processor 36 determines that it has not become the converged state when the distribution $s^2$ of the HF phase difference θ exceeds the first threshold Th1. In the first embodiment, the first threshold Th1 is set to a specific value.

When it is determined that it has become the converged state (step S5: YES), the processor 36 calculates start time that is a time period from the determination that it has become the converged state to the execution until reduction processing is performed at step S8 described later (step S6). In the first embodiment, the processor 36 calculates the start time based on the HF impedance Z at the initial stage at which calculation of the HF impedance Z is started at step S2 (for example, the HF impedance Z calculated first, hereinafter, referred to as initial HF impedance Z).

The initial impedance Z varies according to a type and a size of a target area. For example, when the target area is a fatty tissue, the initial impedance Z is to be relatively large. On the other hand, when the target area is a blood vessel tissue, the initial impedance Z is to be smaller than that of the fatty tissue. Moreover, the initial impedance Z decreases as the size of the target area increases.

That is, at step S6, the processor 36 calculates the start time different depending on the type and the size of a target area. For example, the processor 36 calculates longest time for a fatty tissue as the start time, and calculates second longest time for a blood vessel tissue in a large size as the start time, and calculates shortest time for a blood vessel tissue in a small size as the start time.

After step S6, the processor 36 monitors all the time whether the start time calculated at step S6 has passed (step S7).

When it is determined that the start time has passed (step S7: YES), the processor 36 performs the reduction processing to reduce an output of the high frequency voltage and the high frequency current to the first and the second electrodes 12, 15 from the power source 31 at the time when the start time has passed (step S8). In the first embodiment, the processor 36 stops the operation of the power source 31, that is, performs the reduction processing to stop the output of the high frequency voltage and the high frequency current to the first and the second electrodes 12, 15 from the power source 31.

After step S8, the processor 36 causes the informing unit 37 to inform of information indicating that the incision of the target area has been completed (step S9).

Thereafter, the processor 36 finishes this control flow.

According to the first embodiment explained above, following effects are produced.

In the first embodiment, the processor 36 determines whether it has become the converged state, in other words, whether incision of a target area has been completed by using a "variation (distribution $s^2$) of the HF phase difference θ" that is not affected by a variation of detection by the detecting circuit 34, or a variation of a capacity component of the electric cable C that connects the control device 3 and the treatment instrument 2. The processor 36 performs the reduction processing when determined that it has become the converged state (when determined that the incision of the target area has been completed).

Therefore, according to the first embodiment, completion of incision of a target area can be accurately detected, and excessive heat damage of a living tissue and wear of the treatment instrument 2 can be suppressed.

Furthermore, in the first embodiment, the processor 36 sequentially calculates the initial impedance Z based on the HF voltage signal and the HF current signal output from the detecting circuit 34 and transmitted through the ADC 35, and determines whether the HF impedance Z is equal to or smaller than the second threshold Th2. When it is determined that the initial impedance Z is equal to or smaller than the second threshold Th2, the processor 36 does not perform the reduction processing even when it has determined to have become the converged state.

That is, because the converged state is present also in the initial stage of application of the high frequency energy to a target area, by ignoring the converged state at the initial stage, completion of incision of the target area can be appropriately detected.

Moreover, in the first embodiment, the processor 36 sets the time period (start time) from the determination that it has become the converged state based on the HF impedance Z until the reduction processing is performed.

Therefore, it is possible to apply the high frequency energy to the target area for time (start time) according to a type and a size of the target area, and to treat the target area appropriately according to the type and the size of the target area.

First Modification of First Embodiment

In the first embodiment described above, the processor 36 monitors all the time whether the HF impedance Z exceeds the second threshold Th at step S4, but it is not limited thereto. For example, the processor monitors all the time whether the HF phase difference θ has become equal to or smaller than a third threshold Th3 (FIG. 5) (whether the HF phase difference θ exceeds the third threshold Th3 when the HF phase difference θ is expressed by angle) at step S4. In FIG. 5, the third threshold Th3 is expressed by Cos θ for convenience of explanation. The processor 36 then sequentially performs step S5 and later when it is determined that the HF phase difference θ has become equal to or smaller than the third threshold Th3. In other words, the processor 36 does not perform the reduction processing even when it has become the converged state, when the HF phase difference θ exceeds the third threshold Th3.

Also when step S4 is performed as in the first modification, effects similar to those of the first embodiment described above can be produced.

Second Embodiment

Next, a second embodiment will be explained.

In the following explanation, identical reference symbols are assigned to components identical to the first embodiment described above, and detailed explanation thereof will be omitted or simplified.

In the first embodiment, the first threshold Th1 is set uniformly to a specific value irrespective of a state of tension (grabbing force) applied to a target area by the treatment instrument 2.

On the other hand, in the second embodiment, the processor 36 determines a state of tension applied to a target area by the treatment instrument 2, and sets the first threshold Th1 based on a determination result of the state of tension.

Figure 7A:
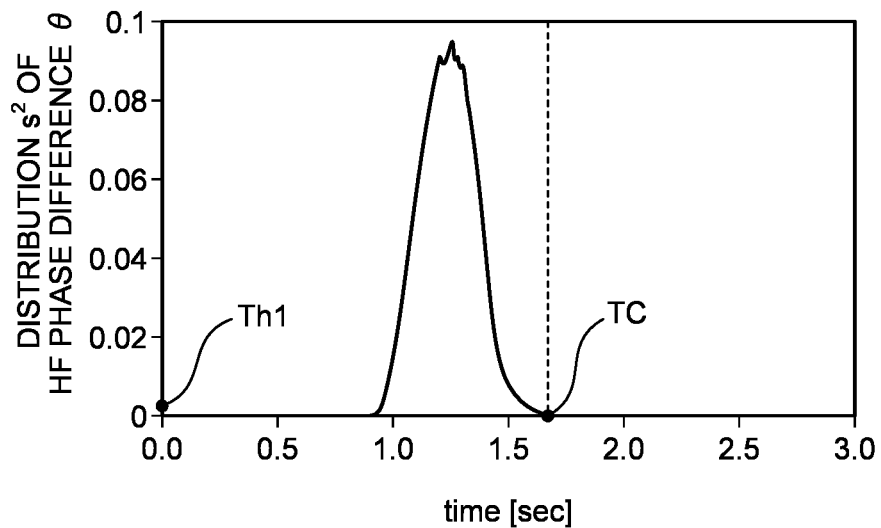
FIGS. 7A and 7B are diagrams explaining a setting method of a first threshold according to an exemplary embodiment.
Figure 7B:
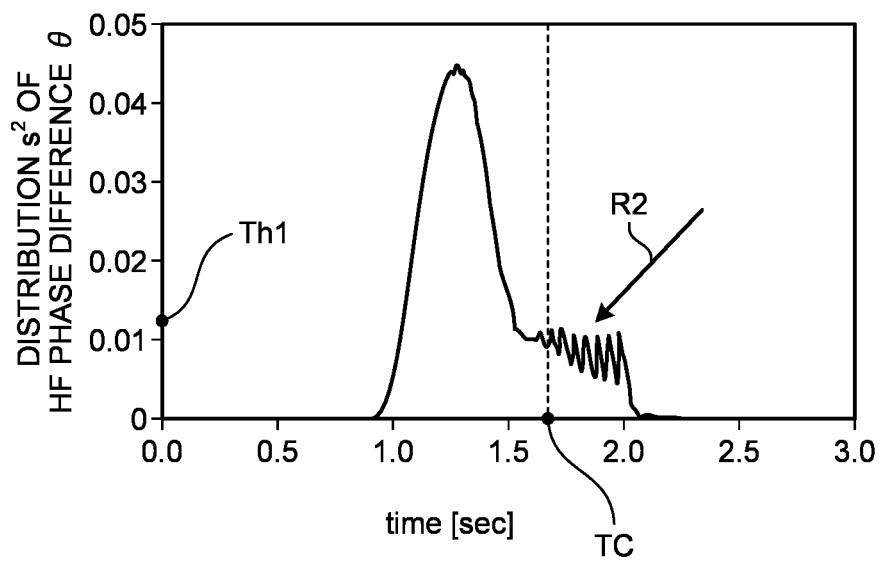
Figure 8A:
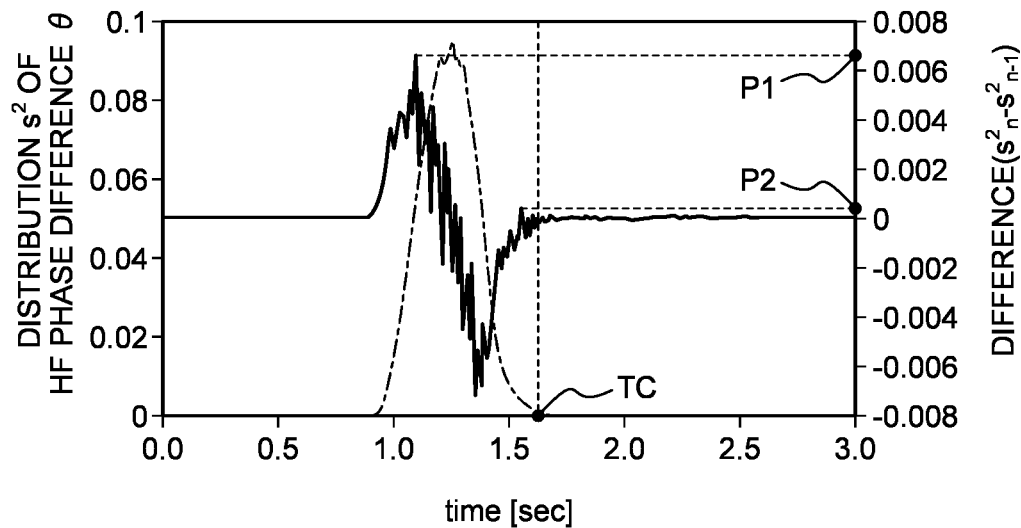
FIGS. 8A and 8B are diagrams explaining a setting method of the first threshold according to the exemplary embodiment of FIGS. 7A and 7B.
Figure 8B:
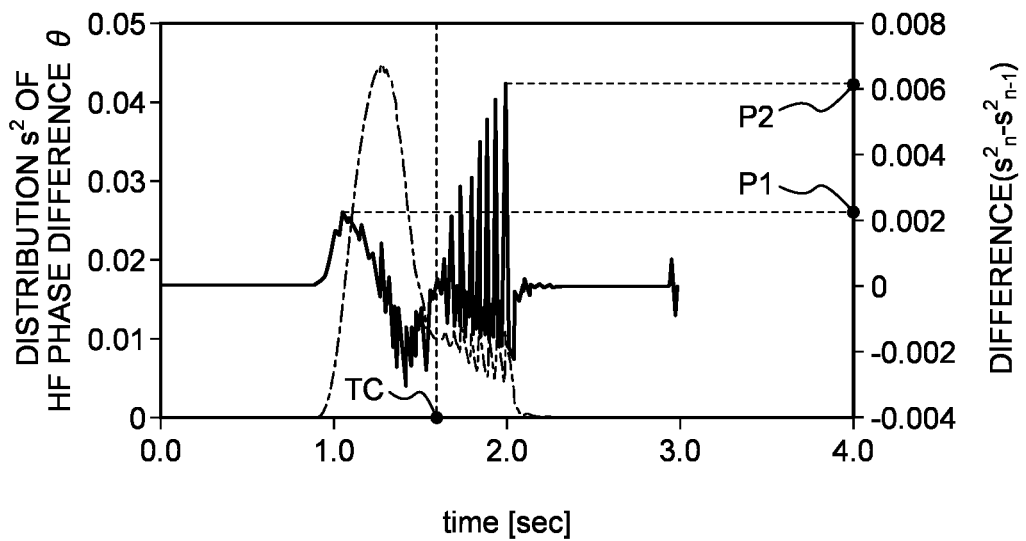

FIGS. 7A, 7B, 8A, and 8B are diagrams explaining a setting method of the first threshold Th1 according to the second embodiment. Specifically, FIGS. 7A and 7B are diagrams showing a behavior of the distribution $s^2$ of the HF phase difference θ at the time of performing the control method illustrated in FIG. 4 similarly to FIG. 6. FIG. 7A shows a behavior of the distribution $s^2$ of the HF phase difference θ when the control method illustrated in FIG. 4 is performed in a state in which normal tension is applied to a target area by the treatment instrument 2 in a normal state. FIG. 7B shows a behavior of the distribution $s^2$ of the HF phase difference θ when the control method illustrated in FIG. 4 is performed in a first state in which tension higher than the normal state is applied to the target area by the treatment instrument 2. In FIG. 8A, the behavior of the distribution $s^2$ of the HF phase difference θ shown in FIG. 7A is indicated by a dot-and-dash line, and a behavior of a difference calculated from the distribution $s^2$ of the HF phase difference θ is indicated by solid line. In FIG. 8B, a behavior of the distribution $s^2$ of the HF phase difference θ shown in FIG. 7B is indicated by a dot-and-dash line, and a behavior of a difference calculated from the distribution $s^2$ of the HF phase difference θ is indicated by a solid line.

The difference described above is a difference $(s^2_n - s^2_{n-1})$ between an n-th distribution $s^2_n$ of the HF phase difference θ at the current time and an n−1-th distribution $s^2_{n-1}$ of the HF phase difference θ.

Because high tension is applied in the first state, a target area is incised suddenly. At this time, because the target area is incised suddenly, water is to remain in the target area without evaporating. As a result of the water repeating evaporation locally although the target area is incised, in the distribution $s^2$ of the HF phase difference θ, abrupt peaks indicating evaporation of the water repeatedly appear after a large peak as indicated by an arrow R2 in FIG. 7B. In this case, in the difference $(s^2_n - s^2_{n-1})$ between the n-th distribution $s^2_n$ of the HF phase difference θ at the current time and the n−1-th distribution $s^2_{n-1}$ of the HF phase difference θ, a peak value P2 after the large peak of the distribution $s^2$ of the HF phase difference θ ends is larger than a peak value P1 before the peak ends as shown in FIG. 8B. In the normal state, the difference $(s^2_n - s^2_{n-1})$ has the peak value P1 larger than the peak value P2 as shown in FIG. 8A.

In the second embodiment, the processor 36 sequentially calculates the difference $(s^2_n - s^2_{n-1})$ between the n-th distribution $s^2_n$ of the HF phase difference θ at the current time and the n−1-th distribution $s^2_{n-1}$ of the HF phase difference θ as shown in FIGS. 8A and 8B. The processor 36 then compares the peak value P1 and the peak value P2, and determines that it is in the first state when the peak value P2 is larger than the peak value P1. On the other hand, the processor 36 determines that it is in the normal state when the peak value P1 is larger than the peak value P2.

When determining that it is in the first state, the processor 36 sets the first threshold Th1 to a higher value than that of the case determined as the normal state (FIGS. 7A and 7B).

According to the second embodiment explained above, in addition to effects similar to those of the first embodiment described above, following effects are obtained.

In the second embodiment, the processor 36 sequentially calculates the difference $(s^2_n - s^2_{n-1})$ between the n-th distribution $s^2_n$ of the HF phase difference θ at the current time and the n−1-th distribution $s^2_{n-1}$ of the HF phase difference θ, and determines a state of tension applied to a target area by the treatment instrument 2 based on a behavior of the difference $(s^2_n - s^2_{n-1})$. When determining that it is in the first state, the processor 36 sets the first threshold Th1 to a higher value than that of the case determined as the normal state.

Therefore, in the first state, it is possible to avoid delay in detecting completion of incision of a target area because of an influence of remaining water.

Third Embodiment

Next, a third embodiment will be explained.

In the following explanation, identical reference symbols are assigned to components identical to the first embodiment described above, and detailed explanation thereof will be omitted or simplified.

In the first embodiment, the first threshold Th1 is uniformly set to a specific value irrespective of a state of tension (grabbing force) applied to a target area by the treatment instrument 2.

On the other hand, in the third embodiment, the processor 36 determines a state of tension applied to a target area by the treatment instrument 2, and sets the first threshold Th1 based on a determination result of the state of tension.

In the third embodiment, the processor 36 respectively determines the normal state and the first state as a state of tension applied to a target area by the treatment instrument 2, similarly to the second embodiment described above.

Figure 9:
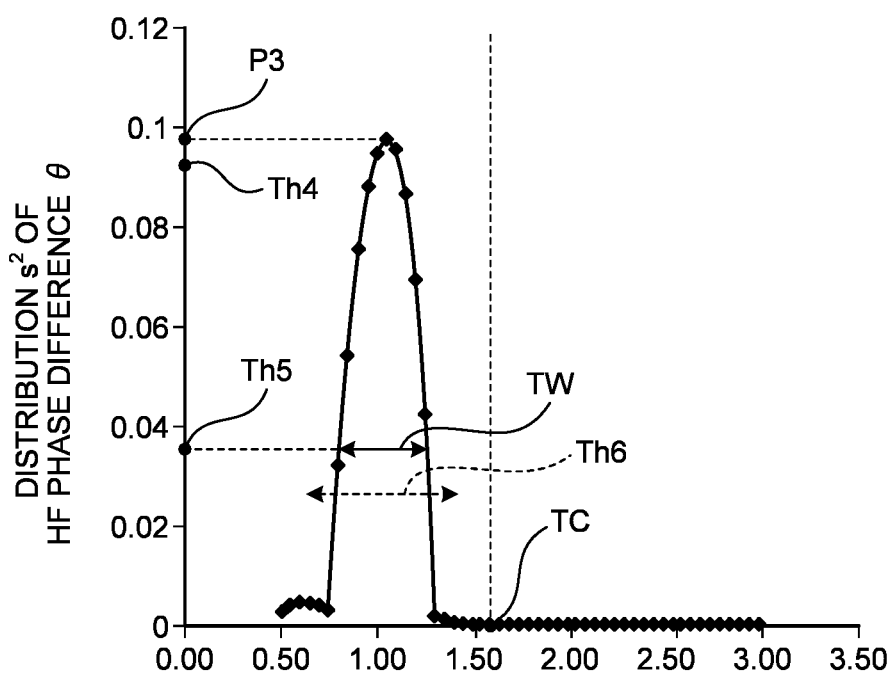
FIG. 9 is a diagram explaining a setting method of the first threshold according to an exemplary embodiment.

FIG. 9 is a diagram explaining a setting method of the first threshold Th1 according to the third embodiment. Specifically, FIG. 9 is a diagram corresponding to FIG. 6.

Because the target area is incised suddenly in the first state, a peak value P3 (FIG. 9) of the distribution $s^2$ of the HF phase difference $\theta$ takes a relatively large value, and is to be equal to or larger a fourth threshold Th4 (FIG. 9). On the other hand, in the normal state, the peak value P3 takes a relatively small value, and is to be smaller than the fourth threshold Th4.

In the third embodiment, the processor 36 compares the peak P3 with the fourth threshold Th4, and determines that it is in the first state when the peak value P3 is equal to or larger than the fourth threshold Th4. On the other hand, when the peak value P3 is smaller than the fourth threshold Th4, the processor 36 determines that it is in the normal state.

When determining that it is in the first state, the processor 36 sets the first threshold Th1 to a larger value than that in the case determined as the normal state.

Also when the normal state and the first state are determined using the peak value P3 as in the third embodiment explained above, effects similar to those of the second embodiment described above can be produced.

Second Modification of Third Embodiment

Because a target area is suddenly incised in the first state, time TW (FIG. 9) from when the distribution $s^2$ of the HF phase difference $\theta$ reaches a fifth threshold Th5 (FIG. 9) until when it reaches the fifth threshold Th5 is relatively short time, and is equal to or smaller than a sixth value Th6. On the other hand, in the normal state, the time TW is to be relatively long time, and exceeds the sixth threshold Th6.

In the third embodiment described above, the normal state and the first state may be determined by using the time TW described above.

Specifically, the processor 36 compares the time TW and the sixth threshold Th6, and determines that it is in the first state when the time TW is equal to or smaller than the sixth threshold Th6. On the other hand, the processor 36 determines that it is in the normal state when the time TW exceeds the sixth threshold Th6.

Also when the normal state and the first state are determined using the time TW as in the second modification explained above, effects similar to those of the third embodiment described above can be produced.

Fourth Embodiment

Next, a fourth embodiment will be explained.

In the following explanation, identical reference symbols are assigned to components identical to the first embodiment described above, and detailed explanation thereof will be omitted or simplified.

In the first embodiment, the first threshold Th1 is set uniformly to a specific value irrespective of a state of tension (grabbing force) applied to a target area by the treatment instrument 2.

On the other hand, in the fourth embodiment, the processor 36 determines a state of tension applied to a target area by the treatment instrument 2, and sets the first threshold Th1 based on a determination result of the state of tension.

In the fourth embodiment, the processor 36 respectively determines the normal state and the first state as a state of tension applied to a target area by the treatment instrument 2, similarly to the second embodiment described above.

Figure 10A:
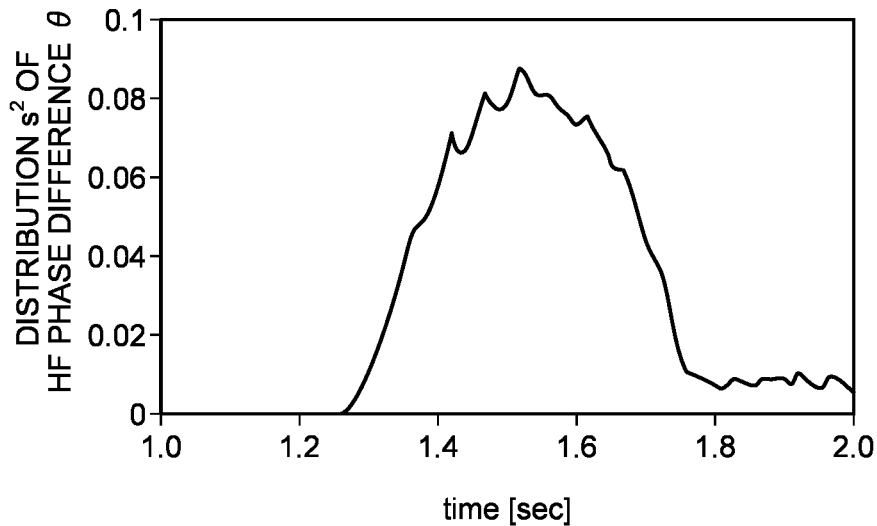
FIGS. 10A and 10B are diagrams explaining a setting method of the first threshold according to an exemplary embodiment.
Figure 10B:
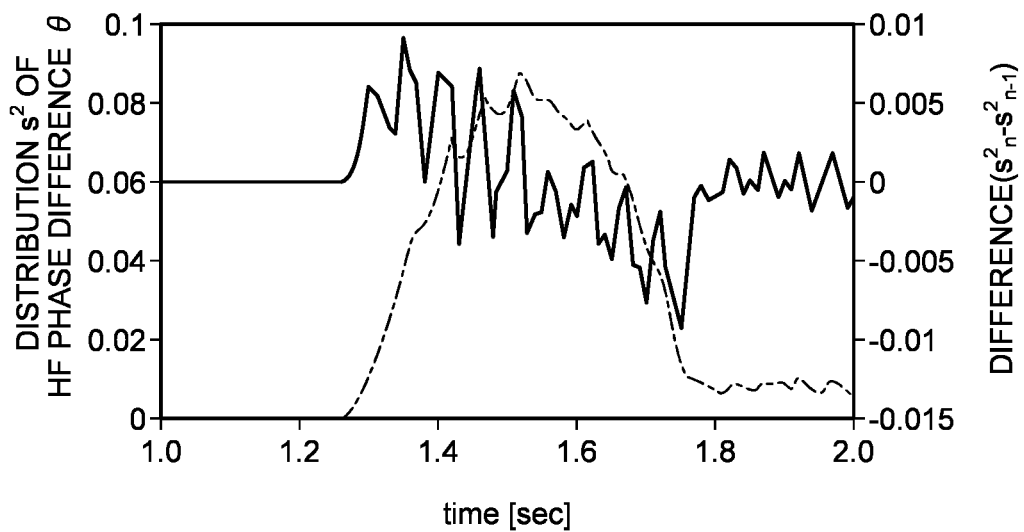

FIGS. 10A and 10B are diagrams explaining a setting method of the first threshold Th1 according to the fourth embodiment. Specifically, FIG. 10A shows a behavior of the distribution $s^2$ of the HF phase difference $\theta$ when the control method illustrated in FIG. 4 is performed in the first state. In FIG. 10B, a behavior of the distribution $s^2$ of the HF phase difference $\theta$ shown in FIG. 10A is indicated by a dot-and-dash line, and the difference $(s^2_n-s^2_{n-1})$ calculated from the distribution $s^2$ of the HF phase difference $\theta$ is indicated by a solid line similarly to FIGS. 8A and 8B.

Because the target area is incised suddenly, incision of the target area and evaporation of water are to occur at the same time. Therefore, the distribution $s^2$ of the HF phase difference $\theta$ shows a behavior in a curved line with noises as shown in FIG. 10A. In this case, the difference $(s^2_n-s^2_{n-1})$ between the n-th distribution $s^2_n$ of the HF phase difference $\theta$ at the current time and the n−1-th distribution $s^2_{n-1}$ of the HF phase difference $\theta$ fluctuates above and below "0" before the distribution $s^2$ of the HF phase difference $\theta$ reaches its peak. In the normal state, because the distribution $s^2$ of the HF phase difference $\theta$ does not include noises (FIG. 7A), the difference $(s^2_n-s^2_{n-1})$ does not fluctuate above and below "0" before the distribution $s^2$ of the HF phase difference $\theta$ reaches its peak.

In the fourth embodiment, the processor 36 sequentially calculates the difference $(s^2_n-s^2_{n-1})$ between the n-th distribution $s^2_n$ of the HF phase difference $\theta$ at the current time and the n−1-th distribution $s^2_{n-1}$ of the HF phase difference $\theta$ as shown in FIG. 8A and FIG. 10B. The processor 36 determines that it is in the first state when the difference $(s^2_n-s^2_{n-1})$ fluctuates above and below "0" before the distribution $s^2$ of the HF phase difference $\theta$ reaches its peak. On the other hand, the processor 36 determines that it is in the normal state when the difference $(s^2_n-s^2_{n-1})$ does not fluctuate above and below "0" before the HF phase difference $\theta$ reaches its peak.

When determining that it is in the first state, the processor 36 sets the first threshold Th1 to a higher value than that of the case determined as the normal state.

Also when the normal state and the first state are determined by determining whether the difference $(s^2_n-s^2_{n-1})$ fluctuates above and below "0" as in the fourth modification explained above, effects similar to those of the second embodiment described above can be produced.

Fifth Embodiment

Next, a fifth embodiment will be explained.

In the following explanation, identical reference symbols are assigned to components identical to the first embodiment described above, and detailed explanation thereof will be omitted or simplified.

In the first embodiment, the first threshold Th1 is set uniformly to a specific value irrespective of a state of tension (grabbing force) applied to a target area by the treatment instrument 2.

On the other hand, in the fifth embodiment, the processor 36 determines a state of tension applied to a target area by the treatment instrument 2, and sets the first threshold Th1 based on a determination result of the state of tension.

Figure 11A:
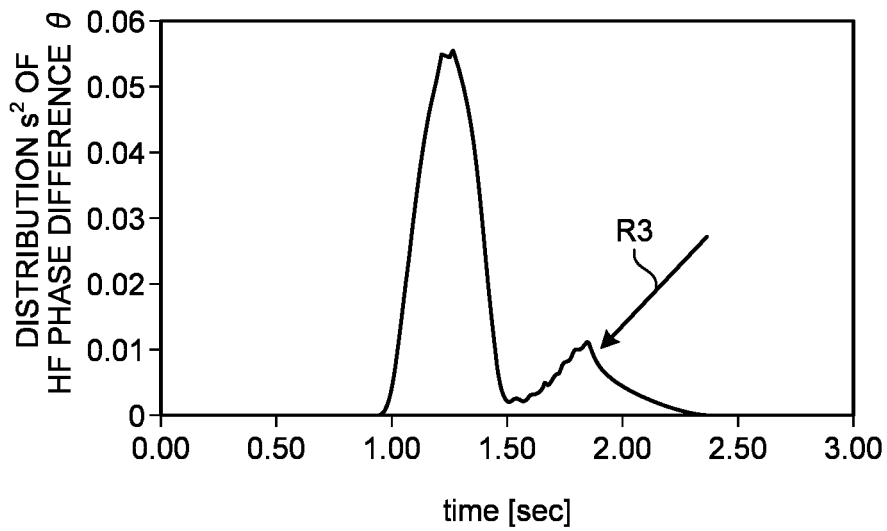
FIGS. 11A and 11B are diagrams explaining a setting method of the first threshold according to an exemplary embodiment.
Figure 11B:
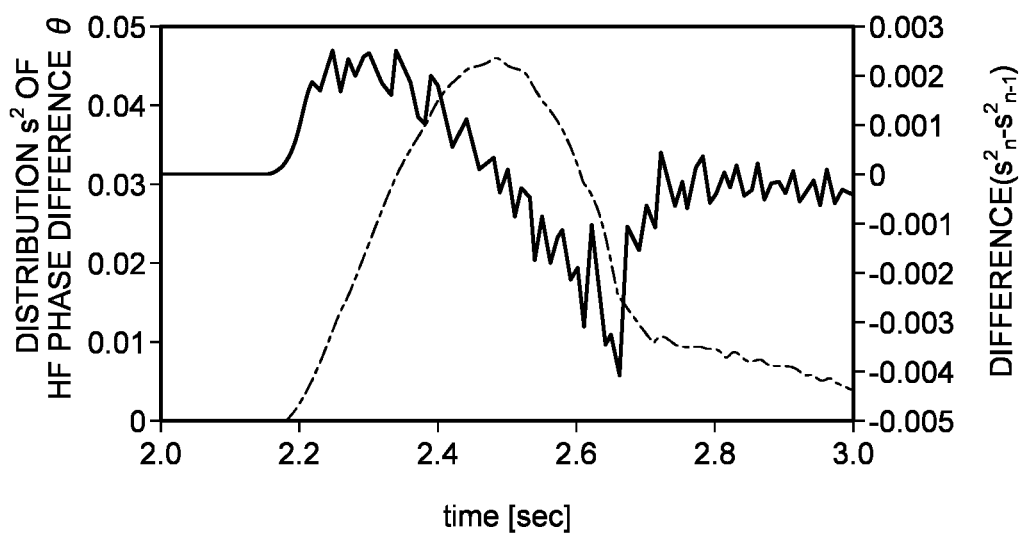

FIGS. 11A and 11B are diagrams explaining a setting method of the first threshold Th1 according to the fifth embodiment. Specifically, FIG. 11A shows a behavior of the distribution $s^2$ of the HF phase difference $\theta$ when the control method illustrated in FIG. 4 is performed in a second state in which tension lower than that in the normal state is applied to a target area by the treatment instrument 2. In FIG. 11B, the behavior of the distribution $s^2$ of the HF phase difference $\theta$ shown in FIG. 11A is indicated by a dot-and-dash line, and a behavior of a difference $(s^2_n - s^2_{n-1})$ calculated from the distribution $s^2$ of the HF phase difference $\theta$ is indicated by solid line, similarly to FIGS. 8A and 8B.

In the second state, because a low tension is applied, a target area is incised gradually. Therefore, in the distribution $s^2$ of the HF phase difference $\theta$, a gentle peak occurs after a large peak as indicated by an arrow R3 in FIG. 11A. In this case, in the difference $(s^2_n - s^2_{n-1})$ between the n-th distribution $s^2_n$ of the HF phase difference $\theta$ at the current time and the n−1-th distribution $s^2_{n-1}$ of the HF phase difference $\theta$, the peak value P1 before the large peak of the distribution $s^2$ of the HF phase difference $\theta$ ends is larger than the peak value P2 before the peak ends as shown in FIG. 11B. Similarly, the difference $(s^2_n - s^2_{n-1})$ has the peak value P1 larger than the peak value P2 in the normal state as shown in FIG. 8A.

In the fifth embodiment, the processor 36 sequentially calculates the difference $(s^2_n - s^2_{n-1})$ between the n-th distribution $s^2_n$ of the HF phase difference $\theta$ at the current time and the n−1-th distribution $s^2_{n-1}$ of the HF phase difference $\theta$ as shown in FIG. 8A and FIG. 11B. The processor 36 determines that it is in the second state when a small peak occurs after a large peak as a behavior of the distribution $s^2$ of the HF phase difference $\theta$, and the peak value P1 is larger than the peak value P2. On the other hand, the processor 36 determines that it is in the normal state when there is no small peak occurring after a large peak as a behavior of the distribution $s^2$ of the HF phase difference $\theta$, and the peak value P1 is larger than the peak value P2.

When determining that it is in the second state, the processor 36 sets the first threshold Th1 to a lower value than that of the case determined as the normal state.

According to the fifth embodiment, in addition to effects similar to those of the first embodiment described above, following effects are produced.

In the fifth embodiment, the processor 36 determines a state of tension applied to a target area by the treatment instrument 2 based on a behavior of the difference $(s^2_n - s^2_{n-1})$. When determining that the state of tension is in the second state, the processor 36 sets the first threshold Th1 to a lower value than that of the case determined as the normal state.

Therefore, erroneous detection of completion of incision of a target area can be prevented in the second state.

Other Embodiments

Embodiments to implement the disclosure have so far been explained, but the disclosure is not to be limited to the first to the fifth embodiments described above.

Figure 12A:
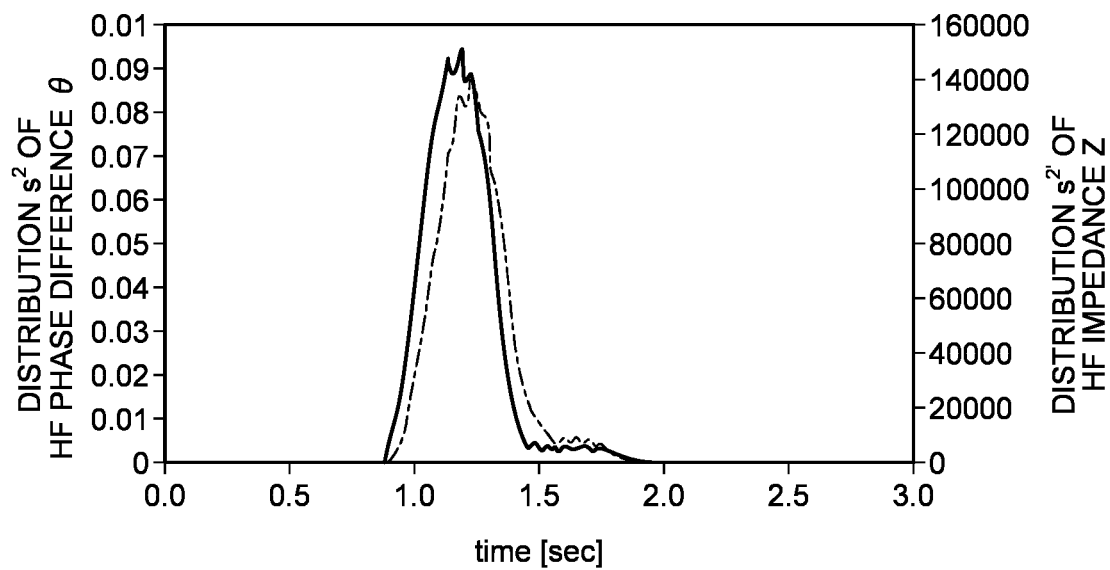
FIGS. 12A and 12B are diagrams illustrating a modification of the exemplary embodiments.
Figure 12B:
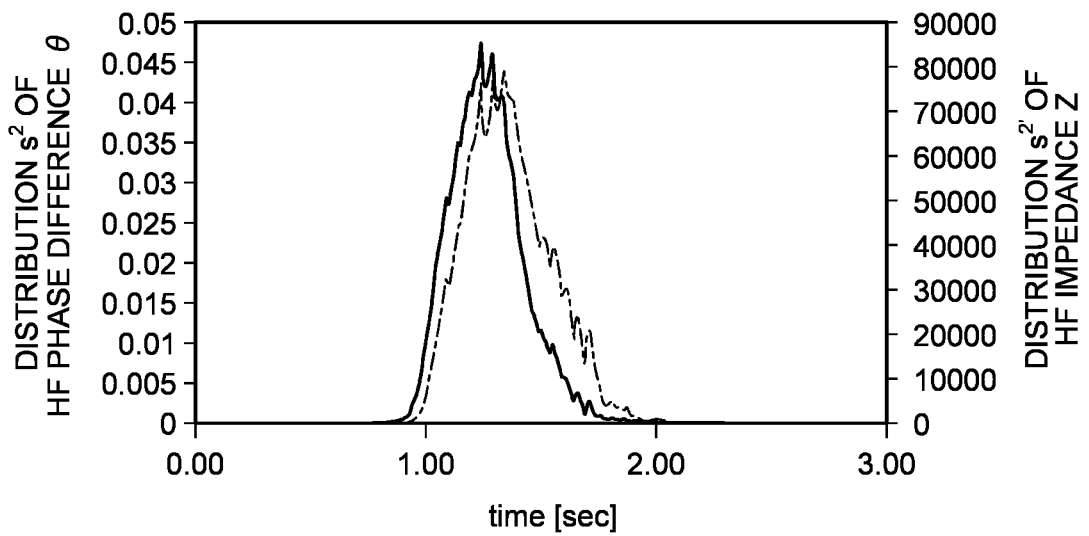

FIG. 12 is a diagram illustrating a third modification of the first to the fifth embodiments. Specifically, in FIG. 12A, a behavior of the distribution $s^2$ of the HF phase difference $\theta$ when the control method illustrated in FIG. 4 is performed in the second state is indicated by a dot-and-dash line, and a behavior of a distribution $s^{2'}$ of the HF impedance Z in this case is indicated by a solid line. In FIG. 12B, a behavior of the distribution $s^2$ of the HF phase difference $\theta$ when the control method illustrated in FIG. 4 is performed in the first state is indicated by a dot-and-dash line, and a behavior of a distribution $s^{2'}$ of the HF impedance Z in this case is indicated by a solid line. The distribution $s^{2'}$ is calculated by using the HF impedance Z instead of the HF phase difference $\theta$ with Equation (1).

As shown in FIGS. 12A and 12B, both when the control method illustrated in FIG. 4 is performed in the first state, and when the control method illustrated in FIG. 4 is performed in the second state, the distribution $s^2$ of the HF phase difference $\theta$ and the distribution $s^{2'}$ of the HF impedance Z show substantially the same behavior. Although illustration is omitted for a case in which the control method illustrated in FIG. 4 is performed in the normal state, the distribution $s^2$ of the HF phase difference $\theta$ and the distribution $s^{2'}$ of the HF impedance Z show substantially the same behavior.

Therefore, at step S5 explained in the first to the fifth embodiments and the first and the second modifications, the distribution $s^{2'}$ of the HF impedance Z may be used instead of the distribution $s^2$ of the HF phase difference $\theta$.

Specifically, the processor 36 determines all the time whether it has become the converged state in which the distribution $s^{2'}$ of the HF has converged by comparing the distribution $s^{2'}$ of the HF impedance Z and a seventh threshold. More specifically, the processor 36 determines that it has become the converged state when the distribution $s^{2'}$ of the HF impedance Z is equal to or smaller than the seventh threshold. On the other hand, the processor 36 determines that it has not become the converged state when the distribution $s^{2'}$ of the HF impedance Z exceeds the seventh threshold.

The seventh threshold may be set uniformly to a specific value. Moreover, the seventh threshold may be set to a value according to a determination result of a state of tension by determining the state of tension (grabbing force) applied to a target area by the treatment instrument 2, using a method substantially the same as the setting method of the first threshold Th1 explained in the second to the fifth embodiments and the second modification (different only in a point in which the distribution $s^{2'}$ of the HF impedance Z is used instead of the distribution $s^2$ of the HF phase difference $\theta$).

Figure 13:
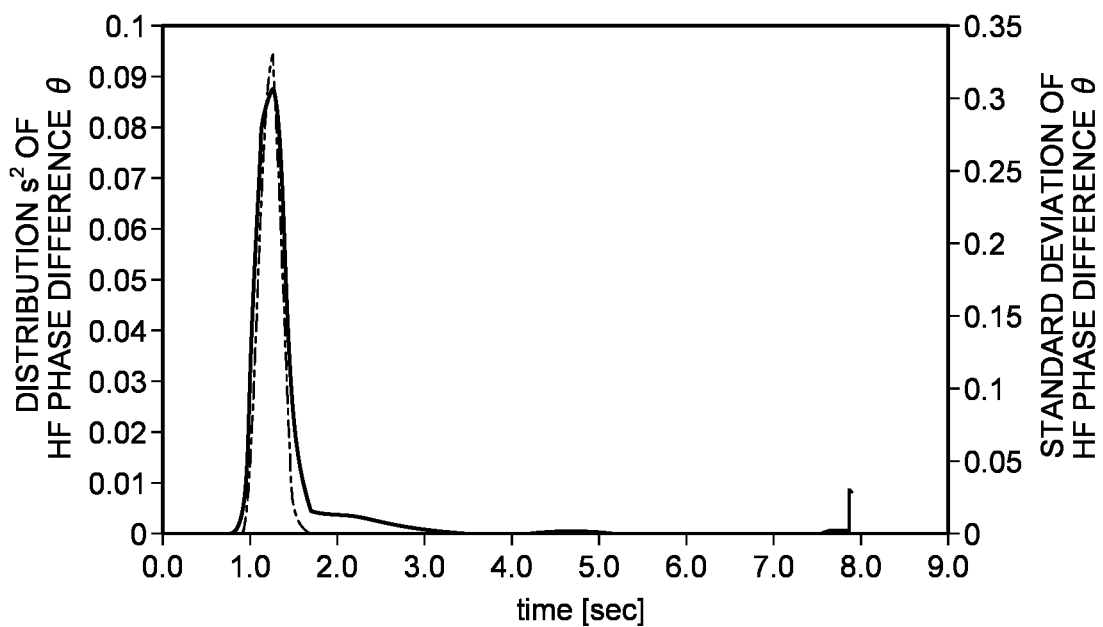
FIG. 13 is a diagram illustrating a modification of the exemplary embodiments.

FIG. 13 is a diagram illustrating a fourth modification of the first to the fifth embodiments. Specifically, in FIG. 13, a behavior of the distribution $s^2$ of the HF phase difference $\theta$ when the control method illustrated in FIG. 4 is performed is indicated by a dot-and-dash line, and a behavior of a standard deviation of the HF phase difference $\theta$ in the case is indicated by a solid line. The standard deviation of the HF phase difference $\theta$ is a positive square root of the distribution $s^2$ of the HF phase difference $\theta$.

As shown in FIG. 13, the distribution $s^2$ of the HF phase difference $\theta$ and the standard deviation of the HF phase difference θ show substantially the same behavior when the control method illustrated in FIG. 4 is performed.

Therefore, at step S5 explained in the first to the fifth embodiments and the first and the second modifications described above, the standard deviation of the HF phase difference θ may be used instead of the distribution $s^2$ of the HF phase difference θ. Moreover, in the setting method of the first threshold Th1 explained in the second to the fifth embodiments and the second modification described above also, the standard deviation of the HF phase difference θ may be used instead of the distribution $s^2$ of the HF phase difference θ. Similarly, at step S5 explained in the third modification, a standard deviation of the HF impedance Z may be used instead of the distribution $s^{2'}$ of the HF impedance Z. Furthermore, in the setting method of the seventh threshold explained in the third modification also, the standard deviation of the HF impedance Z may be used instead of the distribution $s^{2'}$ of the HF impedance Z.

Figure 14:
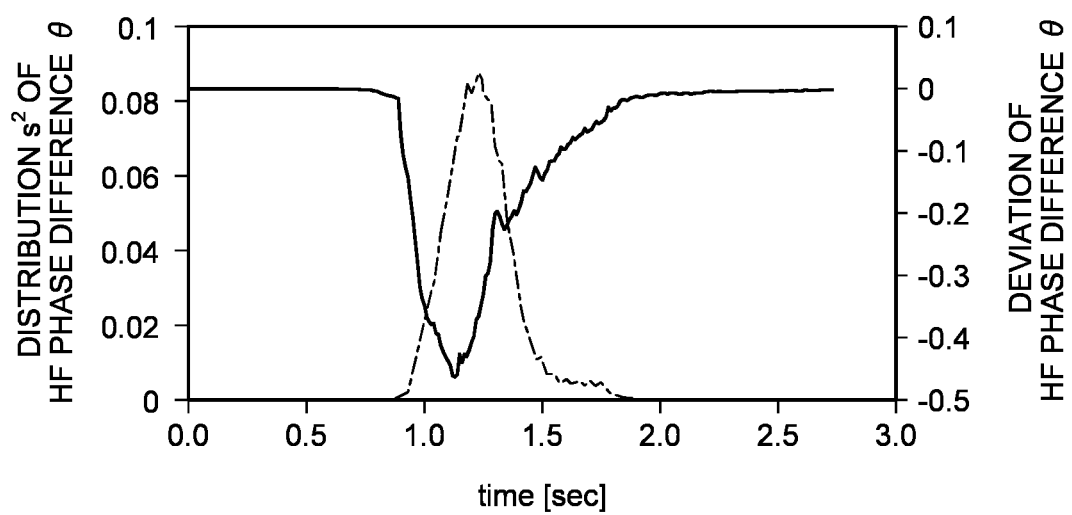
FIG. 14 is a diagram illustrating a modification of the exemplary embodiments.

FIG. 14 is a diagram illustrating a fifth modification of the first to the fifth embodiments. Specifically, in FIG. 14, a behavior of the distribution $s^2$ of the HF phase difference θ when the control method illustrated in FIG. 4 is performed is indicated by a dot-and-dash line, and a behavior of a deviation of the HF phase difference θ in the case is indicated by a solid line. The deviation of an n-th HF phase difference θ($x_n$) at the current time is calculated by following Equation (2). In Equation (2), n signifies the number of data (HF phase difference θ), and is 2 or larger. $x_i$ is a value of each data (HF phase difference θ).

$$\text{DEVIATION} = x_n - \bar{x} \quad (2)$$
$$\bar{x} = \frac{1}{n}\sum_{i=1}^{n} x_i$$

As shown in FIG. 14, distribution $s^2$ of the HF phase difference θ and the deviation of the HF phase difference θ show behaviors in which increases and decreases are opposite when the control method illustrated in FIG. 4 is performed.

Therefore, at step S5 explained in the first to the fifth embodiments and the first and the second modifications described above, the deviation of the HF phase difference θ may be used instead of distribution $s^2$ of the HF phase difference θ. Moreover, in the setting method of the first threshold Th1 explained in the second to the fifth embodiments and the second modification described above also, the deviation of the HF phase difference θ may be used instead of distribution $s^2$ of the HF phase difference θ. Similarly, at step S5 explained in the third modification, a deviation of the HF impedance Z may be used instead of the distribution $s^{2'}$ of the HF impedance Z. The deviation of the HF impedance is calculated with the HF impedance Z instead of the HF phase difference θ by using Equation 2. Furthermore, in the setting method of the seventh threshold explained in the third modification also, the deviation of the HF impedance Z may be used instead of the distribution $s^{2'}$ of the HF impedance Z.

Although a high frequency energy is adopted as a treatment energy to be applied to a target area in the first to the fifth embodiments and the first to the fifth modifications described above, it is not limited thereto, and a thermal energy or an ultrasound energy may be adopted in addition to the high frequency energy. "To apply a thermal energy to a target area" means to cause a heater to transmit generated heat to a target area. Moreover, "to apply an ultrasound energy to a target area" means to apply ultrasound vibrations to a target area.

When a high frequency energy and a thermal energy are adopted as the treatment energy to be applied to a target area, a control described below may be added.

For example, a heater is provided in the first grabbing member 8 out of the first and the second grabbing members 8, 9. The control device 3 supplies an electric power to the heater through a pair of leads (not illustrated) constituting the electric cable C. The electric power supplied to the heater may be a direct current power or an alternating current power. The control device 3 measures a resistance of the heater (hereinafter, denoted as heater resistance) by using, for example, the voltage drop method from a voltage value and a current value supplied to the heater. The control device 3 performs a control to bring the heater resistance to a target resistance value while changing a power to be supplied to the heater, to bring the temperature of the heater (hereinafter, denoted as heater temperature) to a target temperature. That is, heat from the heater controlled to be the target temperature is transmitted to a target area.

Figure 15A:
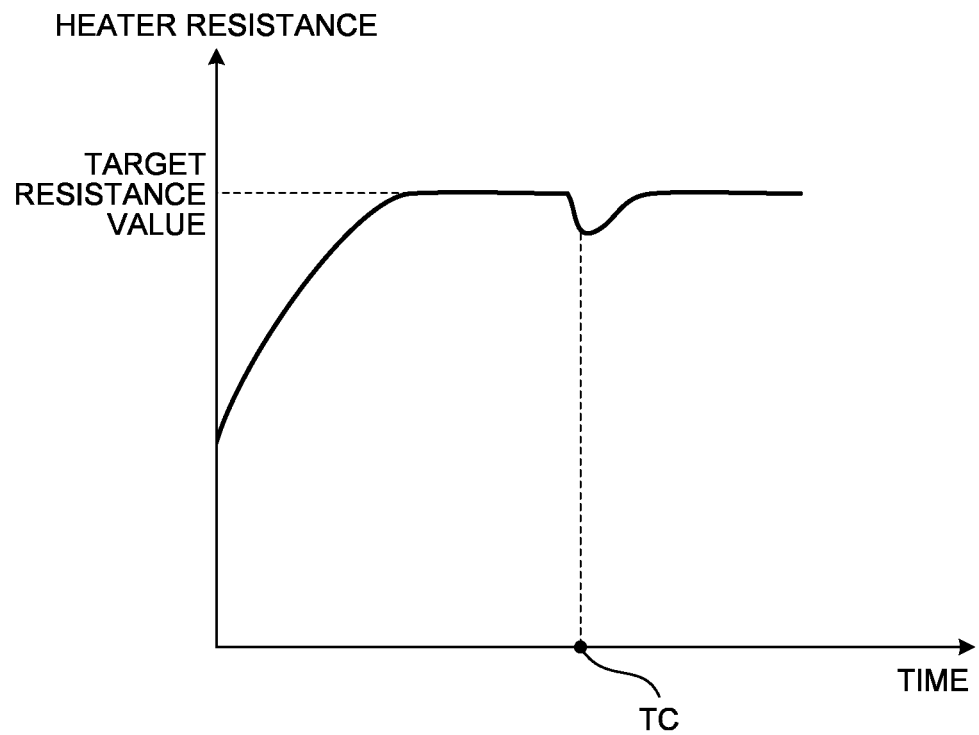
FIGS. 15A and 15B are diagrams illustrating a modification of the exemplary embodiments.
Figure 15B:
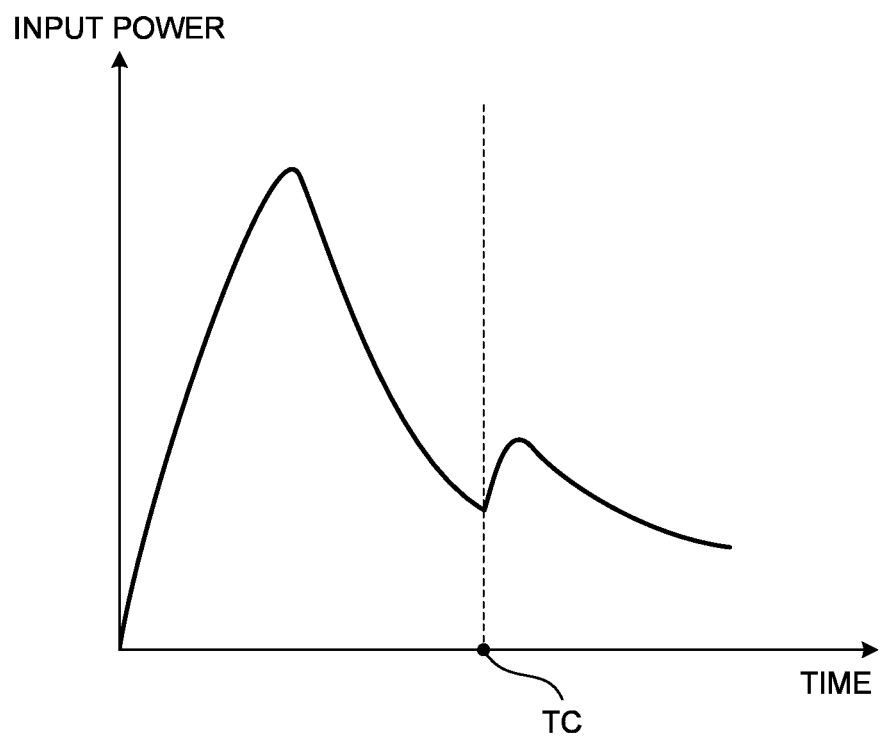
Figure 16A:
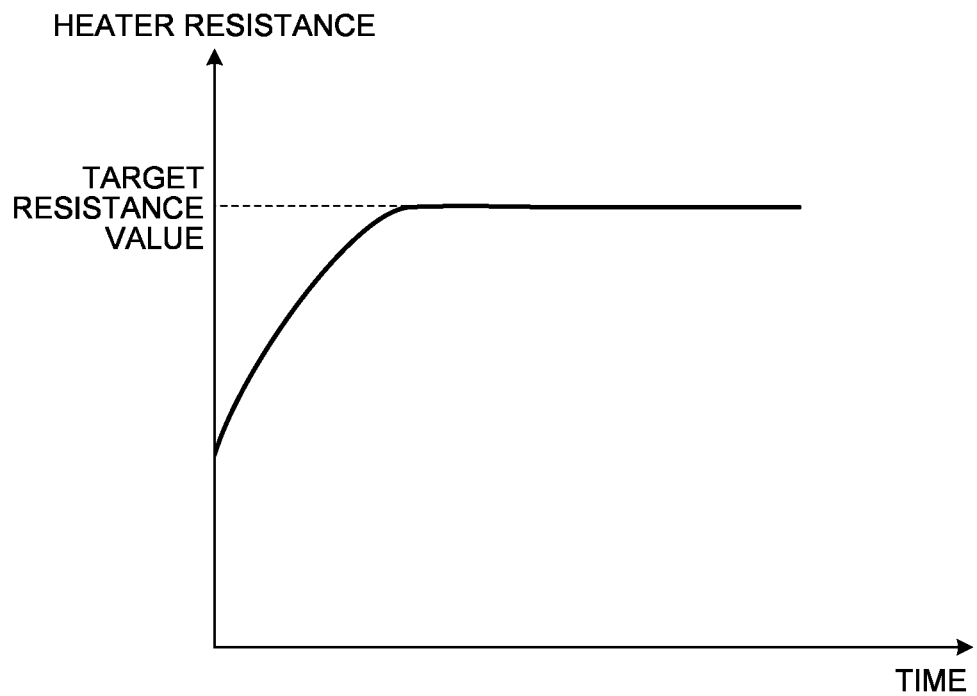
FIGS. 16A and 16B are diagrams illustrating the modification as shown in FIGS. 15A and 15B of the exemplary embodiments.
Figure 16B:
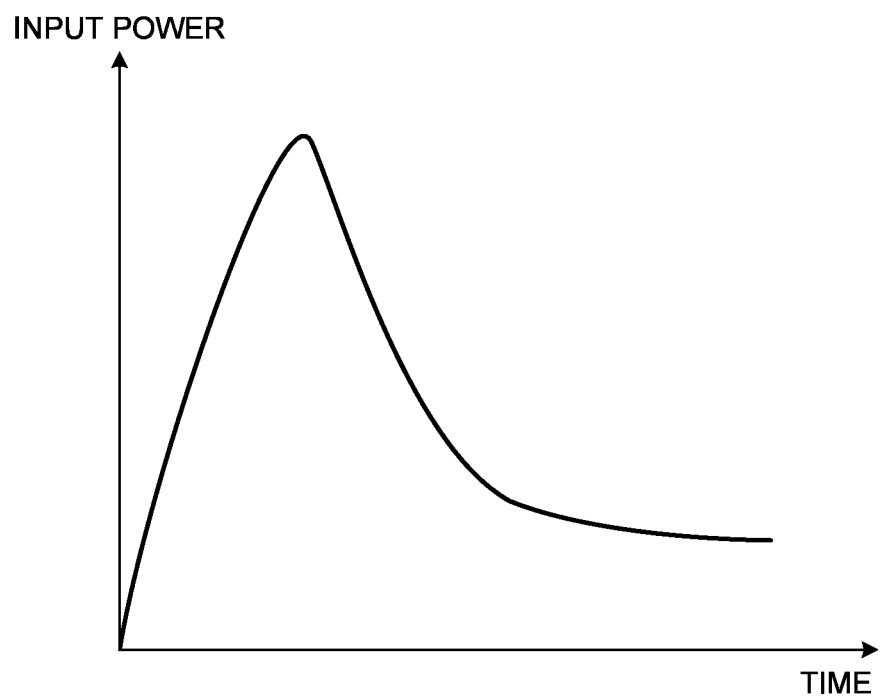

FIGS. 15A, 15B, 16A, and 16B are diagrams illustrating a sixth modification of the first to the fifth embodiments. Specifically, FIGS. 15A and 15B show behaviors of the heater resistance and an input power when a target area is incised. Moreover, FIGS. 16A and 16B show behaviors of a heater resistance and an input power when a target area is not incised.

The input power to the heater shows a behavior having one peak by the control to bring the heater resistance to a target resistance value as shown in FIG. 15B and FIG. 16B.

As is obvious when FIGS. 15A, 15B, 16A, and 16B are compared, when the target area is incised at the time TC (FIGS. 15A and 15B), discontinuous variations occur in the behaviors of the heater resistance and the input power.

Specifically, because the target area is not present between the first and the second electrodes 12 and 15 when the target area is incised, the first and the second electrodes 12 and 15 come into contact with each other. Heat of the first electrode 12 is lost to the second electrode 15, to cause a reduction of temperature of the first electrode 12. The temperature reduction of the first electrode 12 causes a reduction of the heater temperature, and that is, to cause a reduction of the heater resistance. To maintain the heater resistance at the target resistance value, the input power is to be increased, and the input power temporarily increases after the time TC. Because of the above matters, discontinuous variations occur in the behaviors of the heater resistance and the input power at the time TC.

When determining that it has become the converged state at step S5, and that discontinuous variations occur in behaviors of the heater resistance and the input power, the processor 36 determines that a target area has been incised, and performs the reduction processing at step S8.

In the first to the fifth embodiments and the first to the sixth modifications, either one of a distribution, a standard deviation, and a deviation is used as a variation of the HF phase difference θ or the HF impedance Z. The variation converges toward 0 without fluctuating above and below 0 as incision of the target area approaches its completion. Therefore, by comparing the variation with the first threshold Th1 or the like, it is possible to determine that it has become the converged state in which the variation has converged (incision of a target area has completed) easily.

On the other hand, it can be considered to use a difference between the n-th HF phase difference (or the HF impedance)

at the current time and the n−1-th HF phase difference (or the HF impedance). However, the difference converges toward 0 while fluctuating above and below 0 as the incision of a target area approaches its completion. Therefore, it is difficult to set a threshold to determine convergence of the difference (completion of incision of the target area), and if the threshold is set simply, completion of incision of a target area can be erroneously detected.

As described above, by using a variation of the HF phase difference or the HF impedance as in the first to the fifth embodiments and the first to the sixth modifications described above, completion of incision of a target area can be detected with high accuracy.

Although the start time is set according to the initial impedance Z in the first to the fifth embodiments and the first and the sixth modifications described above, not limited thereto, it may be set uniformly to specific start time (including 0 hours).

Moreover, at step S5, a setting to determine as error and suspend the processing may be added when it does not become the converged state even when predetermined time sufficient for completing incision has passed. When it is determined as error, the output of the high frequency voltage and the high frequency current to the treatment instrument 2 is stopped, and the informing unit 37 informs of error information.

Furthermore, although the start time is set according to the initial impedance Z at step S6, it is not limited thereto, and the start time may be set according to a time period from a start of application of the high frequency energy to a target area until the HF impedance Z becomes a value of a minimum value+α.

According to the control device, the treatment system, and the control method according to the disclosure, completion of incision of a living tissue can be detected with high accuracy.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A control device comprising:
    a power source configured to supply a high frequency power to a treatment instrument configured to treat a living tissue;
    a detecting circuit configured to sequentially detect a phase difference between a voltage and a current of the high frequency power supplied to the treatment instrument; and
    a processor configured to control operation of the power source, the processor being configured to:
        sequentially calculate a variation of the phase difference detected by the detecting circuit,
        compare the calculated variation of the phase difference with a first threshold for a variation of a phase difference,
        perform reduction processing to reduce an output of subsequent high frequency power to be supplied to the treatment instrument when the calculated variation of the phase difference is equal to or smaller than the first threshold,
        determine a tension state applied to the living tissue by the treatment instrument, and
        set the first threshold for the variation of the phase difference based on the tension state.

2. The control device according to claim 1, wherein the processor is configured to calculate at least one of a deviation, a standard deviation, or a distribution of the phase difference to determine the variation of the phase difference.

3. The control device according to claim 1, wherein the detecting circuit is further configured to sequentially detect the voltage and the current of the high frequency power supplied to the treatment instrument, and the processor is configured to:
    sequentially calculate an impedance of the living tissue based on the voltage and the current detected by the detecting circuit,
    compare the calculated impedance with a second threshold for an impedance, and
    when the calculated impedance is equal to or smaller than the second threshold, suspend the reduction processing regardless of the calculated variation of the phase difference.

4. The control device according to claim 1, the processor being further configured to:
    compare the detected phase difference with a third threshold for the phase difference, and
    when the detected phase difference exceeds the third threshold, suspend the reduction processing regardless of the calculated variation of the phase difference.

5. The control device according to claim 1, the processor being further configured to:
    sequentially calculate a difference between the variation of the phase difference calculated n-th being a current time and the variation of the phase difference calculated n−1-th, and
    determine the state of the tension based on a behavior of the calculated difference.

6. The control device according to claim 1, wherein the processor is further configured to determine the tension state by comparing a peak value of the variation of the phase difference with a fourth threshold that is set for a peak value of a variation of a phase difference.

7. The control device according to claim 1, wherein the processor is further configured to determine the tension state by comparing a first length of time from when the variation of the phase difference reaches a fifth threshold until the variation reaches the fifth threshold a subsequent time, with a sixth threshold that is a predetermined time.

8. The control device according to claim 1, the processor being further configured to:
    determine a normal state and a first state in which the tension is higher than that in the normal state, as the state of the tension, and
    set the first threshold to a larger value when determining as the first state, than that when determining as the normal state.

9. The control device according to claim 1, wherein the processor is further configured to
    determine the tension state as being a normal state or a second state, the second state being when the tension is lower than that in the normal state, and
    set the first threshold to a smaller value when determining as the second state, than that when determining as the normal state.

10. The control device according to claim 1, the detecting circuit being further configured to sequentially detect the voltage and the current of the high frequency power supplied to the treatment instrument, and
the processor being further configured to:
calculate an impedance of the living tissue based on the voltage and the current detected by the detecting circuit, and
based on the calculated impedance, set a first length of time until the reduction processing is performed from a time that the calculated variation of the phase difference is equal to or smaller than the first threshold.

11. A treatment system comprising:
the control device according to claim 1; and
a treatment instrument configured to apply a high frequency energy to a living tissue by being supplied with a voltage and a current from the control device.

12. A control method that is performed by a processor of a control device, the method comprising:
sequentially calculating a variation of a phase difference of a voltage and a current of a high frequency power supplied to a treatment instrument from a power source;
comparing the calculated variation of the phase difference with a first threshold set for a variation of a phase difference;
performing reduction processing to reduce output of the high frequency power to be supplied to the treatment instrument when the calculated variation of the phase difference is equal to or smaller than the first threshold;
determining a tension state applied to the living tissue by the treatment instrument, and
setting the first threshold for the variation of the phase difference based on the tension state.

* * * * *